United States Patent
Moon et al.

(10) Patent No.: US 8,617,709 B2
(45) Date of Patent: Dec. 31, 2013

(54) FUNCTIONALIZED METAL NANOPARTICLE, BUFFER LAYER INCLUDING THE SAME AND ELECTRONIC DEVICE INCLUDING THE BUFFER LAYER

(75) Inventors: Hyun Sik Moon, Seoul (KR); Jong Jin Park, Yongin-si (KR); Bon Won Koo, Suwon-si (KR); Jung Seok Hahn, Seongnam-si (KR); Do Hwan Kim, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 869 days.

(21) Appl. No.: 12/078,778

(22) Filed: Apr. 4, 2008

(65) Prior Publication Data

US 2008/0299382 A1 Dec. 4, 2008

(30) Foreign Application Priority Data

May 28, 2007 (KR) .................. 10-2007-0051514

(51) Int. Cl.
*B32B 5/16* (2006.01)
(52) U.S. Cl.
USPC ............ 428/403; 428/323; 428/328; 977/788
(58) Field of Classification Search
USPC .................. 428/403–407, 323, 328; 977/788
See application file for complete search history.

(56) References Cited

U.S. PATENT DOCUMENTS

| | | | |
|---|---|---|---|
| 6,208,553 B1 * | 3/2001 | Gryko et al. .................. | 365/151 |
| 6,682,895 B2 * | 1/2004 | Mirkin et al. .................. | 506/16 |
| 6,777,516 B2 * | 8/2004 | Li et al. ......................... | 526/258 |
| 7,323,561 B2 * | 1/2008 | Lindsey et al. ............... | 540/145 |
| 7,491,422 B2 * | 2/2009 | Zhang et al. .................. | 427/256 |
| 2004/0253536 A1 * | 12/2004 | Park et al. .................. | 430/270.1 |
| 2005/0025969 A1 * | 2/2005 | Berning et al. ............... | 428/403 |
| 2005/0058774 A1 * | 3/2005 | Wada ............................ | 427/180 |
| 2005/0129843 A1 | 6/2005 | Wu et al. | |
| 2005/0255237 A1 * | 11/2005 | Zhang et al. .................. | 427/180 |
| 2006/0081835 A1 | 4/2006 | Hutchison et al. | |
| 2007/0089783 A1 | 4/2007 | Jung et al. | |

FOREIGN PATENT DOCUMENTS

| | | |
|---|---|---|
| WO | WO 2004/020453 | 3/2004 |
| WO | WO 2006/001923 | 1/2006 |
| WO | WO 2006/080895 | 8/2006 |
| WO | WO 2006/124769 | 11/2006 |

OTHER PUBLICATIONS

Tam-Chang, Self-Assembled Monolayers on Gold Generated from Alkanethiols with the Structure RNHCOCH2SH, Langmuir (1995), 11, 4371-4382.*

(Continued)

*Primary Examiner* — Hoa (Holly) Lee
(74) *Attorney, Agent, or Firm* — Harness, Dickey & Pierce, P.L.C.

(57) ABSTRACT

Disclosed herein is a functionalized metal nanoparticle, a buffer layer including the functionalized metal nanoparticle, and an electronic device including the buffer layer. The buffer layer including the functionalized metal nanoparticle according to example embodiments may improve the injection of electrons or holes and the charge mobility between layers in the electronic device, may form ohmic contacts, and may improve the selectivity between electrodes and the buffer layer at the time of forming the buffer layer on the electrodes, thereby improving the efficiency of the electronic device.

15 Claims, 2 Drawing Sheets

(56) References Cited

OTHER PUBLICATIONS

Lenk, et al, Structural investigation of molecular organization in self-assembled monolayers of a semifluorinated amidethiol, Langmuir (1994), 10, 4610-4617.*

Biddle, An Introduction to SMS: Self-Assembled Monolayers in Organic Chemistry, Oct. 9, 2001.*

Chechik and Stirling, Gold-thiol self-assembled monolayers, The Chemistry of Organic Derivatives of Gold and Silver, chapter 15, pp. 552-628, 1999).*

Daniel and Astruc, Gold Nanoparticles: Asembly, supramolecular chemistry, quantum-size related properties, and applicatioins toward biology, catalysis, and nanotechnology, Chem. Rev. (2004) 104, 293-346.*

Ovchenkov et al., The electronic structure of metal/aklane thiol self-assembled monolayers/metal junctionis for magnetoelectronics applications, Chem. Phys. Lett. 381:1-2 (Nov. 4, 2003), pp. 7-13.*

European Search Report in corresponding European Application No. 08155875.1 dated Oct. 1, 2008.

Andres et al., "Self-Assembly of a Two-Dimensional Superlattice of Molecularly Linked Metal Clusters", Science, vol. 273 (Sep. 20, 1996).

* cited by examiner

FUNCTIONALIZED METAL NANOPARTICLE, BUFFER LAYER INCLUDING THE SAME AND ELECTRONIC DEVICE INCLUDING THE BUFFER LAYER

PRIORITY STATEMENT

This application claims priority under U.S.C. §119 to Korean Patent Application No. 10-2007-0051514, filed on May 28, 2007, in the Korean Intellectual Property Office (KIPO), the entire contents of which are incorporated herein by reference.

BACKGROUND

1. Field

Example embodiments relate to a functionalized metal nanoparticle, a buffer layer including the functionalized metal nanoparticle and an electronic device including the buffer layer. Other example embodiments relate to a functionalized metal nanoparticle, a buffer layer including the functionalized metal nanoparticle, which may improve the injection and mobility of electrons or holes, may form ohmic contacts, and may improve the selectivity between electrodes and the buffer layer at the time of forming the buffer layer on the electrodes and an electronic device including the buffer layer.

2. Description of the Related Art

Organic material-based device technologies may supplement silicon based electronic devices in the field of relatively large-sized flexible displays. The technologies for manufacturing organic thin film transistors (OTFTs), which are being researched, may be sufficiently competitive in the fields of integrity and performance with silicon thin film transistors.

The infrastructure costs for manufacturing organic thin film transistors (OTFTS) are only about ⅓ of those for manufacturing amorphous silicon thin film transistors, and the organic thin film transistors (OTFTS) may be more easily operated and continuously processed, unlike inorganic substrates. Therefore, the process costs of the organic thin film transistors (OTFTS) are expected to decrease compared to those of conventional thin film transistors. In order to apply the organic thin film transistor (OTFT) to the backplane of a display, the design and synthesis of an organic semiconductor having increased mobility and the improvement of the characteristics of the organic thin film transistor (OTFT) through the design of devices and the development of process technologies are required.

Conventionally, a thin film transistor may include a substrate, a gate electrode, a gate insulation layer, source/drain electrodes and a semiconductor layer, and, if necessary, may further include an electron injection layer, a hole injection layer, an electron transportation layer, and a hole transportation layer.

The characteristics of a thin film transistor are determined by the injection and migration of electrons or holes. Ideally, electrons or holes are effectively injected into a channel layer without contact resistances between electrodes and a semiconductor layer, and the electrons or holes thus rapidly migrate in the channel layer. Unlike silicon thin film transistors, which may easily form ohmic contacts, in organic thin film transistors (OTFTs), the contact resistances between electrodes and a semiconductor layer may become a main cause of the deterioration of the characteristics thereof. Generally, when metals come into contact with a semiconductor layer or a charge transportation layer, having a relatively low impurity concentration, a potential barrier may be formed at the interface therebetween, so that resistance values may become increased. In principle, the height of a potential barrier may depend on the mismatch of the energy level between electrodes and a semiconductor or between electrodes and a charge transportation layer and the adhesion state therebetween.

In the contact resistances between electrodes and a semiconductor layer or between electrodes and a charge transportation layer, conventional electrode surface treatment methods used to decrease the contact resistances between electrodes and a semiconductor layer or between electrodes and a charge transportation layer include a technology of treating an electrode surface using a self-assembled monolayer (SAM) and/or a technology of treating an electrode surface using a buffer layer. Among these technologies, the technology of treating an electrode surface using a buffer layer includes forming a layer including materials for decreasing the contact resistances between electrodes and a semiconductor layer or between electrodes and a charge transportation layer, and this technology may be mainly applied to organic thin film transistors (OTFTs) or organic light emitting diodes (OLEDs).

As these buffer layer materials, low-molecular semiconductors which may be formed into a film in a vacuum process, e.g., triphenyl amine derivatives, or acid-doped conductive polymers which may be formed into a film in a solution process, e.g., poly(3,4-ethylenedioxythiophene) poly(styrenesulfonate), have been used.

Buffer layer materials that may be formed into a film in a solution process allow for cost reduction. However, when the acid-doped conductive polymers are used as the buffer layer materials, acid-dopants may be diffused to channel layers, thus decreasing the stability of the device.

With most hole transportation (P type) organic semiconductors, because the highest occupied molecular orbital (HOMO) level of organic material is above about 5.0 eV, gold (Au), having a work function of about 5.0 eV or lower, may be used for source/drain electrodes in order to form ohmic contacts. However, gold (Au) is expensive and may not be patterned well, and not suitable for use as the source/drain electrodes of the backplane of a display. As an alternative to gold (Au), research into the use of indium tin oxide (ITO) for source/drain electrodes is being conducted. However, indium tin oxide (ITO) has a work function of about 4.8 eV or lower, and the degree of the mismatch of the energy level between electrodes and a semiconductor layer is greater than that in the case of using gold (Au) for source/drain electrodes.

SUMMARY

Accordingly, example embodiments provide a functionalized metal nanoparticle. Example embodiments also provide a buffer layer including the functionalized metal nanoparticle, which may improve the injection and mobility of electrons or holes, may improve the selectivity between electrodes and the buffer layer at the time of forming the buffer layer on the electrodes, and may form ohmic contacts. Example embodiments also provide an electronic device including the buffer layer.

Example embodiments provide a functionalized metal nanoparticle represented by Formula 1 below:

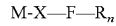  [Formula 1]

wherein M is a metal atom selected from the group consisting of gold (Au), silver (Ag), copper (Cu), palladium (Pd) and platinum (Pt),
X is sulfur (S) or a cyano group (CN), F is a functionalized group selected from the group consisting of an adhesion-enhancing functionalized group, a hole-injection functionalized group, a hole-transportation functionalized group, an electron injection functionalized group, and an electron transportation functionalized group, R is a reactive group that can be covalently bonded with electrodes composed of metal oxides, and n is an integer of about 0 or about 1.

In example embodiments, the functionalized metal nanoparticle, represented by the above Formula 1, may have a structure represented by Formula 2 below:

$$M-X-F \qquad \text{[Formula 2]}$$

wherein M is a metal atom selected from the group consisting of gold (Au), silver (Ag), copper (Cu), palladium (Pd) and platinum (Pt), X is sulfur (S) or a cyano group (CN), and F is a functionalized group selected from the group consisting of an adhesion-enhancing functionalized group, a hole-injection functionalized group, a hole-transportation functionalized group, an electron injection functionalized group, and an electron transportation functionalized group.

Example embodiments provide a buffer layer including the functionalized metal nanoparticle represented by the above Formula 1, which may improve the injection and mobility of electrons or holes, and may form ohmic contacts.

Further, example embodiments provide a buffer layer including the functionalized metal nanoparticle represented by the above Formula 2, which may improve the selectivity between electrodes and the buffer layer at the time of forming the buffer layer on the electrodes. Example embodiments provide an electronic device including the buffer layer.

BRIEF DESCRIPTION OF THE DRAWINGS

Example embodiments will be more clearly understood from the following detailed description taken in conjunction with the accompanying drawings.

FIG. 1 is a graph showing the results of thermal gravimetric analysis (TGA) of a functionalized metal nanoparticle synthesized in Preparation Example 2 according to example embodiments;

FIG. 2 is a schematic sectional view showing a diode-like device manufactured in Example 1 according to example embodiments; and FIG. 3 is a graph showing current-voltage characteristic curves of diode-like devices in Example 1 and Comparative Example 1.

Figure 1:
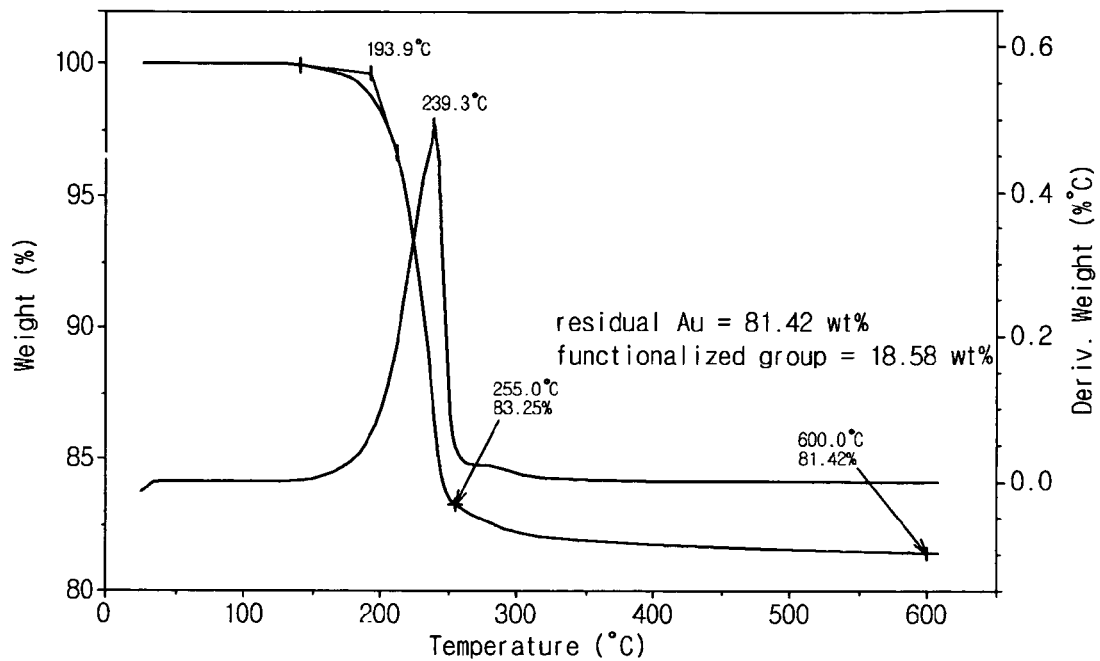
FIGS. 1-3 represent non-limiting example embodiments described herein.

It should be noted that these figures are intended to illustrate the general characteristics of methods, structures and/or materials utilized in certain example embodiments and to supplement the written description provided below. These drawings are not, however, to scale, and may not precisely reflect the precise structural or performance characteristics of any given embodiment, and should not be interpreted as defining or limiting the range of values or properties encompassed by the example embodiments. In particular, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION OF EXAMPLE EMBODIMENTS

Hereinafter, example embodiments will be described in detail with reference to the attached drawings. Example embodiments may, however, be embodied in many different forms and should not be construed as being limited to the embodiments set force herein. Rather, these embodiments are provided so that this disclosure will be thorough and complete, and will fully convey the scope of example embodiments to those skilled in the art.

In the drawings, the thickness of layers and regions are exaggerated for clarity. It will also be understood that when an element such as a layer, region or substrate is referred to as being "on" or "onto" another element, it may lie directly on the other element or intervening elements or layers may also be present. Like reference numerals refer to like elements throughout the specification.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Example embodiments provide a functionalized metal nanoparticle represented by Formula 1 below:

M-X—F—R$_n$  [Formula 1]

wherein M is a metal atom selected from the group consisting of gold (Au), silver (Ag), copper (Cu), palladium (Pd) and platinum (Pt),
X is sulfur (S) or a cyano group (CN),
F is a functionalized group selected from the group consisting of an adhesion-enhancing functionalized group, a hole-injection functionalized group, a hole-transportation functionalized group, an electron injection functionalized group, and an electron transportation functionalized group,
R is a reactive group that can be covalently bonded with electrodes composed of metal oxides, and
n is an integer of about 0 or about 1.

Further, in example embodiments, the functionalized metal nanoparticle, represented by the above Formula 1, may have a structure represented by Formula 2 below:

M-X—F  [Formula 2]

wherein M is a metal atom selected from the group consisting of gold (Au), silver (Ag), copper (Cu), palladium (Pd) and platinum (Pt),
X is sulfur (S) or a cyano group (CN), and
F is a functionalized group selected from the group consisting of an adhesion-enhancing functionalized group, a hole-injection functionalized group, a hole-transportation functionalized group, an electron injection functionalized group, and an electron transportation functionalized group.

In the above Formula 1 or 2, the F may be selected from the group consisting of substituted or unsubstituted alkyl groups of about 1 to about 20 carbon atoms; oxadiazole compounds; porphyrin compound derivatives including N,N'-diphenyl-N,N'-di(3-methylphenyl)-4,4'-diaminobiphenyl, N,N'-diphenyl-N,N'-dinaphthyl-4,4'-diaminobiphenyl, and N,N,N',N'-tetraphenyl-21H,23H-porphyrin; triarylamine derivatives including polymers having aromatic tertiary amines in main chains or side chains thereof, 1,1-bis(4-di-p-tolylaminophenyl)cyclohexane, N,N,N-tri(p-tolyl)amine, and 4,4',4'-tris[N-(3-methylphenyl)-N-phenylamino]trimethylamine; carbazole derivatives including N-phenylcarbazole and polyvinylcarbazole; phthalocyanine derivatives including nonmetallic phthalocyanine and copper phthalocyanine; starburst amine derivatives; enamine stilbene derivatives; derivatives of aromatic tertiary amine-containing styryl amine compounds; spirobifluorenyl anthracene; tetrafluorene; thiophene; aniline; pyrrole; and phenylene vinylene, but is not limited thereto.

Further, in the above Formula 1 or 2, the substituted alkyl groups may be represented by Formulas 3 to 5 below:

(CH$_2$CH$_2$O)$_n$  [Formula 3]

wherein n is an integer of about 1 to about 5.

(CH$_2$)$_n$-A$_1$-(CH$_2$)$_n$  [Formula 4]

wherein A$_1$ is selected from the group consisting of O, S, a carbonyl group, an ester group, a carbonyl amine group, and an ester amine group, and
n is an integer of about 1 to about 10.

(CH$_2$)$_n$-A$_1$-(CH$_2$)$_n$-A$_2$-(CH$_2$)$_n$  [Formula 5]

wherein A$_1$ and A$_2$ are each independently selected from the group consisting of O, S, a carbonyl group, an ester group, a carbonyl amine group, and an ester amine group, and
n is an integer of about 1 to about 10.

However, the substituted alkyl groups are not limited thereto. Further, in the above Formula 1, the R may be selected from the group consisting of a trimethoxysilane group (—Si(OCH$_3$)$_3$), a trichlorosilane group (—SiCl$_3$), a phosphate group (—PO$_3$$^-$) and —P(O)(OH)$_2$, but is not limited thereto.

Further, example embodiments provide a functionalized metal nano particle represented by Formula 6 or 7 below:

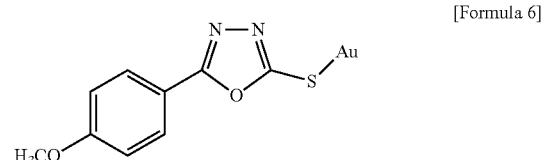

[Formula 6]

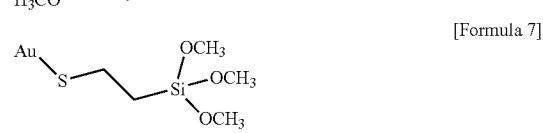

[Formula 7]

Example embodiments provide a buffer layer including the functionalized metal nanoparticle. For example, a buffer layer including the functionalized metal nanoparticle represented by Formula 1 below according to example embodiments:

M-X—F—R$_n$  [Formula 1]

wherein M is a metal atom selected from the group consisting of gold (Au), silver (Ag), copper (Cu), palladium (Pd) and platinum (Pt),
X is sulfur (S) or a cyano group (CN),
F is a functionalized group selected from the group consisting of an adhesion-enhancing functionalized group, a hole-injection functionalized group, a hole-transportation functionalized group, an electron injection functionalized group, and an electron transportation functionalized group,
R is a reactive group that can be covalently bonded with electrodes composed of metal oxides, and
n is an integer of about 0 or about 1.

When the buffer layer including the functionalized metal nanoparticle represented by the above Formula 1 is applied to the electrode surface of an electronic device, the injection of electrons or holes between an electrode and a semiconductor layer or between an electrode and a charge transportation layer and the charge mobility therebetween may be improved, and the electrical characteristics of an electronic device may be improved by forming ohmic contacts.

Further, example embodiments provide a buffer layer including the functionalized metal nanoparticle represented by Formula 2 below according to example embodiments:

M-X—F  [Formula 2]

wherein M is a metal atom selected from the group consisting of gold (Au), silver (Ag), copper (Cu), palladium (Pd) and platinum (Pt), X is sulfur (S) or a cyano group (CN), and F is a functionalized group selected from the group consisting of an adhesion-enhancing functionalized group, a hole-injection functionalized group, a hole-transportation functionalized group, an electron injection functionalized group, and an electron transportation functionalized group.

When the buffer layer including the functionalized metal nanoparticle represented by the above Formula 2 is applied to the electrode surface of an electronic device, the selectivity between an electrode and the buffer may be improved at the time of forming the buffer layer on the electrode, and thus the buffer layer blocking the migration of electrons or holes between electrodes may be overcome, thereby improving the electrical characteristics of an electronic device.

In the above Formula 1 or 2, the F may be selected from the group consisting of substituted or unsubstituted alkyl groups of about 1 to about 20 carbon atoms; oxadiazole compounds; porphyrin compound derivatives including N,N'-diphenyl-N, N'-di(3-methylphenyl)-4,4'-diaminobiphenyl, N,N'-diphenyl-N,N'-dinaphthyl-4,4'-diaminobiphenyl, and N,N,N',N'-tetraphenyl-21H,23H-porphyrin; triarylamine derivatives including polymers having aromatic tertiary amines in main chains or side chains thereof, 1,1-bis(4-di-p-tolylaminophenyl)cyclohexane, N,N,N-tri (p-tolyl)amine, and 4,4',4'-tris[N-(3-methylphenyl)-N-phenylamino]trimethylamine; carbazole derivatives including N-phenylcarbazole and polyvinylcarbazole; phthalocyanine derivatives including nonmetallic phthalocyanine and copper phthalocyanine; starburst amine derivatives; enamine stilbene derivatives; derivatives of aromatic tertiary amine-containing styryl amine compounds; spirobifluorenyl anthracene; tetrafluorene; thiophene; aniline; pyrrole; and phenylene vinylene, but is not limited thereto.

Further, in the above Formula 1 or 2, the substituted alkyl groups may be represented by Formulas 3 to 5 below:

$(CH_2CH_2O)_n$ [Formula 3]

wherein n is an integer of about 1 to about 5.

$(CH_2)_n\text{-}A_1\text{-}(CH_2)_n$ [Formula 4]

wherein $A_1$ is selected from the group consisting of O, S, a carbonyl group, an ester group, a carbonyl amine group, and an ester amine group, and n is an integer of about 1 to about 10.

$(CH_2)_n\text{-}A_1\text{-}(CH_2)_n\text{-}A_2\text{-}(CH_2)_n$ [Formula 5]

wherein $A_1$ and $A_2$ are each independently selected from the group consisting of O, S, a carbonyl group, an ester group, a carbonyl amine group, and an ester amine group, and n is an integer of about 1 to about 10.

However, the substituted alkyl groups are not limited thereto. Further, in the above Formula 1, the R may be selected from the group consisting of a trimethoxysilane group (—Si(OCH$_3$)$_3$), a trichlorosilane group (—SiCl$_3$), a phosphate group (—PO$_3^-$), and —P(O)(OH)$_2$, but is not limited thereto.

Further, example embodiments provide a buffer layer including the functionalized metal nanoparticle represented by Formula 6 or 7 below according to example embodiments:

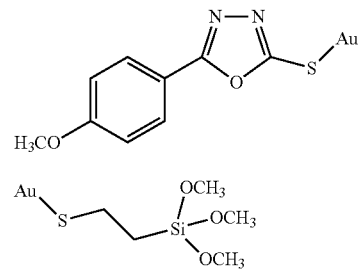

These buffer layers according to example embodiments may be formed in the form of a thin film using typical methods commonly used in the related field. For example, the buffer layer may be formed as a thin film by dissolving the functionalized metal nanoparticle in an organic solvent and using typical coating methods.

The organic solvent may be determined by those skilled in the art by suitably selecting a high-solubility solvent depending on the structure and kind of specific buffer materials, and may include, but is not limited to, alcohols including methyl alcohol, ethyl alcohol, n-propyl alcohol, isopropyl alcohol, n-butyl alcohol, sec-butyl alcohol, t-butyl alcohol, isobutyl alcohol, and diacetone alcohol; ketones including acetone, methylethyl ketone, and methylisobutyl ketone; glycols including ethylene glycol, diethylene glycol, triethylene glycol, propylene glycol, butylene glycol, hexylene glycol, 1,3-propanediol, 1,4-butanediol, 1,2,4-butanetriol, 1,5-pentanediol, 1,2-hexanediol, and 1,6-hexanediol; glycol ethers including ethylene glycol monomethyl ether and triethylene glycol monoethyl ether; glycol ether acetates including propylene glycol monomethyl ether acetate (PGMEA); acetates including ethyl acetate, butoxyethoxy ethyl acetate, butyl carbitol acetate (BCA), and dihydroterpineol acetate (DHTA); terpineols; trimethyl pentanediol monoisobutyrate (TEXANOL); dichloroethane (DCE); chlorobenzene; xylene; N-methyl-2-pyrrolidone(NMP); and mixtures thereof.

Methods of forming the buffer layer may include, but are not limited to, spin coating, dip coating, roll coating, screen coating, spray coating, spin casting, flow coating, screen printing, ink jetting and/or drop casting.

The amount of the buffer material added may be determined by those skilled in the art through suitable selection according to the use and case thereof, and may be in the range of about 0.01 to about 10 parts by weight, based on about 100 parts by weight of a solvent. At the time of a thin film formation test, when the concentration of the buffer material is above about 10 wt %, forming a relatively uniform thin film may be difficult because the concentration thereof may be relatively high.

The buffer layer formed through these processes may be a monolayer, or may have a thickness ranging from about 0.01 nm to about 100 nm, but is not limited thereto, and may be suitably adjusted depending on the use and case thereof by those skilled in the art. Example embodiments provide an electronic device including the buffer layer, for example, an electronic device including the buffer layer on the electrode surface thereof.

When the buffer layer according to example embodiments is layered on the surface of electrodes, the contact resistance values between the electrode and a semiconductor layer or between the electrode and a charge transportation layer may be increased, so that ohmic contacts may be formed, and the injection of electrons or holes, which are carriers, and the charge migration between the layers may be accelerated, with the result that an electronic device including the buffer layer exhibits improved electrical characteristics.

In example embodiments, the "electronic device" refers to an electronic part using the conduction of electrons in solid. The electronic device, which may be used in example embodiments, may include, but is not limited to, an organic thin film transistor (OTFT), an organic light emitting diode (OLED), a solar cell and/or an organic photovoltaic conversion device.

Specifically, when the buffer layer according to example embodiments is applied to an organic thin film transistor, the organic thin film transistor may include a substrate, a gate electrode, a gate insulation film, source/drain electrodes, a buffer layer and an organic semiconductor layer. The organic thin film transistor may have a structure in which the buffer layer is formed on the gate electrode or the source/drain electrodes.

The organic thin film transistor may have a bottom contact structure, a top contact structure and/or a top gate structure, and, moreover, may have a modified structure according to the intended purpose. Further, in the electronic device according to example embodiments, constituents other than the buffer layer may be formed using materials and methods commonly used in the related technical field.

For example, in the case of the organic thin film transistor, the substrate may include glass, silicon and/or plastic. The gate electrode or source/drain electrodes may include metals, conductive polymers, and metal oxides. For example, the gate electrode or source/drain electrodes may include, but are not limited to, gold (Au), silver (Ag), aluminum (Al), nickel (Ni), molybdenum (Mo), tungsten (W), indium-tin oxide (ITO), polythiophene, polyaniline, polyacetylene, polypyrrole, polyphenylene vinylene, a mixture of PEDOT (polyethylene-dioxythiophene)/PSS (polystyrenesulfonate) and/or indium-zinc oxide (IZO).

Further, the gate insulation film may include, but is not limited to, organic materials, e.g., polyolefin, polyvinyl, polyacrylate, polystyrene, polyurethane, polyimide, polyvinylphenol, and mixtures thereof, and inorganic materials, e.g., $SiN_x(0<x<4)$, $SiO_2$ and $Al_2O_3$. The organic semiconductor layer may include, but is not limited to, pentacene, tetracene, copper phthalocyanine, polythiophene, polyaniline, polyacetylene, polypyrrole, polyphenylenevinylene and derivatives thereof.

Meanwhile, when the buffer layer according to example embodiments is applied to an organic light emitting diode, the organic light emitting diode may include a substrate, a cathode, a buffer layer, a light emitting layer (EML), a electron transportation layer (ETL) and an anode. The organic thin film transistor may have a structure in which the buffer layer is formed on the gate electrode or the source/drain electrodes. Constituents other than the buffer layer may also be formed using materials and methods commonly used in the related technical field.

Hereinafter, example embodiments will be described in detail with reference to Examples. These Examples are set forth to illustrate example embodiments, but should not be construed to be the limit of example embodiments.

PREPARATION EXAMPLE 1

Synthesis of Functionalized Metal Nano Particle
(Represented by the Above Formula 1, and n is 0)

About 0.5 g (about 1.47 mmol) of hydrogen tetrachloroaurate was dissolved in about 150 ml of diluted water, and then a solution obtained by dissolving about 1.6 g (about 2.94 mmol) of tetraoctylammonium bromide in about 400 ml of toluene was added thereto and was then uniformly mixed for about 1 hour using a magnetic bar to form a first mixed solution. Subsequently, a solution obtained by dissolving about 0.31 g (about 1.47 mmol) of 5-(4-Methoxyphenyl)-1, 3,4-oxadiazole-2-thiol in about 50 ml of dimethylformamide (DMF) was uniformly dropped into the first mixed solution using a dropping funnel and then was mixed for about 1 hour to form a second mixed solution. Next, a solution obtained by dissolving about 0.55 g of $NABH_4$ in about 120 ml of diluted water was dropped into the second mixed solution, thereby preparing a functionalized metal nanoparticle, which is a synthetic material (represented by Formula 6 below) substituted with 5-(4-Methoxyphenyl)-1,3,4-oxadiazole on the surface of gold nanoparticle thereof.

[Formula 6]

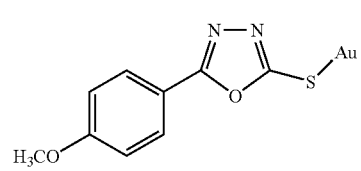

PREPARATION EXAMPLE 2

Synthesis of Functionalized Metal Nano Particle
(Represented by the Above Formula 1, and n is 1)

About 0.5 g (about 1.47 mmol) of hydrogen tetrachloroaurate was dissolved in about 150 ml of diluted water, and then a solution obtained by dissolving about 1.6 g (about 2.94 mmol) of tetraoctylammonium bromide in about 400 ml of toluene was added thereto and was then uniformly mixed for about 1 hour using a magnetic bar to form a first mixed solution. Subsequently, a solution obtained by dissolving about 0.28 g (about 1.47 mmol) of (3-mercaptopropyl)trimethoxysilane in about 50 ml of dimethylformamide (DMF) was uniformly dropped into the first mixed solution using a dropping funnel, and was then mixed for about 1 hour to form a second mixed solution. Next, a solution obtained by dissolving about 0.55 g of $NABH_4$ in about 120 ml of diluted water was dropped into the second mixed solution, thereby preparing a functionalized metal nanoparticle, which is a synthetic material (represented by Formula 7 below) substituted with a trimethoxysilane group on the surface of a gold nanoparticle thereof.

[Formula 7]

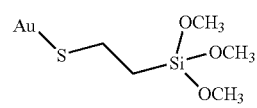

The result of thermal gravimetric analysis (TGA) of the functionalized metal nanoparticle synthesized in Preparation Example 2 is shown in FIG. 1. Referring to the TGA result in FIG. 1, it is inferred that, because, at a temperature of about 600° C., the weight ratio of residual Au to the original functionalized metal particle synthesized in Preparation Example 2 was about 81.42%, the weight ratio of functionalized groups present on the surface of Au to the original functionalized metal particle synthesized in Preparation Example 2 was about 18.58%. For this reason, the functionalized groups present on the surface of Au contribute to the improvement of the injection and mobility of charges, compared with the fact that the weight of pure Au was not changed up to a temperature of about 60° C. in the TGA result.

EXAMPLE 1

Figure 2:
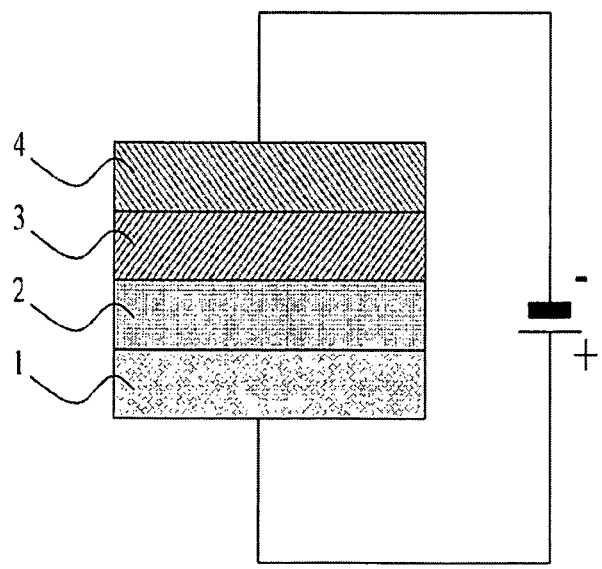

Manufacture of Diode-Like Device Including Buffer Layer Formed of Functionalized Metal Nanoparticle As shown in FIG. 2, a buffer layer 2 having a thickness of about 5 nm was formed on a patterned ITO glass substrate, which is a first electrode 1, at a speed of about 1000 rpm using a spin coating method by dissolving about 0.1 mg of the functionalized metal nanoparticle synthesized in Preparation Example 1 in about 10 mg of xylene. Subsequently, an organic semiconductor layer 3 having a thickness of about 70 nm was formed by thermally depositing pentacene at a vacuum of about $10^{-6}$ Torr, and then Au, which is a second electrode 4, was thermally deposited on the organic semiconductor layer 3 to a thickness of about 70 nm, thereby manufacturing a diode-like device.

COMPARATIVE EXAMPLE 1

A diode-like device was manufactured using the same method as in Example 1, except that a buffer layer was not formed.

EXPERIMENTAL EXAMPLE

Figure 3:
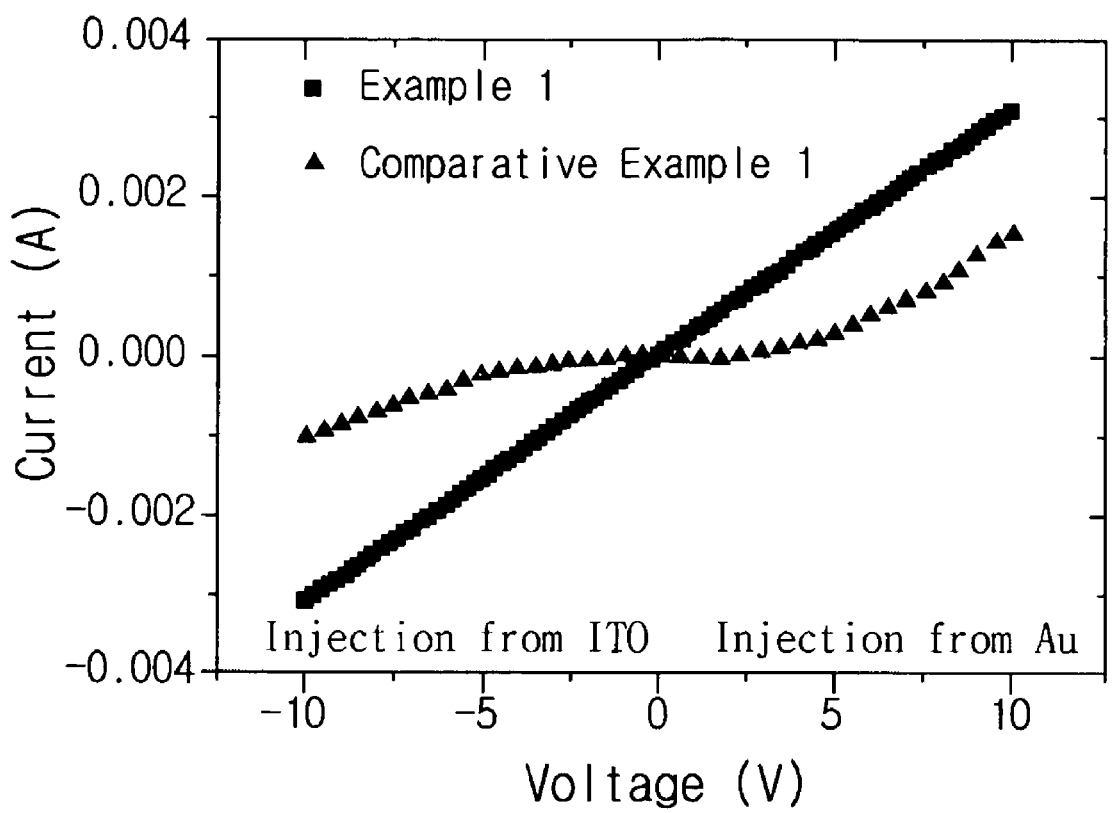

The current-voltage characteristics of diode-like devices in Example 1 and Comparative Example 1 were respectively evaluated, and were shown in FIG. 3. In order to evaluate the effect of injecting holes into channel layers in ITO, which may be used for a backplane for a large-sized display henceforth, the current change thereof was evaluated while a (+) electrode was connected to ITO, a (−) electrode was connected to Au, and voltage was increased.

Referring to FIG. 3, ohmic contacts were formed in Example 1, in which a buffer layer including a functionalized metal nanoparticle was formed, compared to Comparative Example 1, in which the buffer layer was not formed. For this reason, the adhesivity between ITO and pentacene was improved through the buffer layer including the functionalized metal nanoparticle, the injection and mobility of charges was improved by matching the energy level of the buffer layer with that of pentacene, and ohmic contacts were formed.

The functionalized metal nanoparticle according to example embodiments provides a buffer layer which may improve the injection of electrons or holes and the charge mobility between layers, and may improve the selectivity between electrodes and the buffer layer at the time of forming the buffer layer on the electrodes. Further, the electronic device including the buffer layer according to example embodiments may accelerate the injection of electrons or holes and the charge migration between layers, may improve the efficiency thereof by forming ohmic contacts, and may exhibit improved electrical characteristics.

As described above, although example embodiments have been disclosed for illustrative purposes, those skilled in the art will appreciate that various modifications, additions and substitutions are possible, without departing from the scope and spirit of example embodiments as disclosed in the accompanying claims.

What is claimed is:

1. A functionalized metal nanoparticle represented by Formula 1:

M-X—F—R$_n$ [Formula 1]

wherein M is a metal atom selected from the group consisting of gold (Au), silver (Ag), copper (Cu), palladium (Pd) and platinum (Pt), X is sulfur (S) or a cyano group (CN), F is selected from the group consisting of ethyl groups; oxadiazole compounds; porphyrin compound derivatives including N,N'-diphenyl-N,N'-di(3-methylphenyl)-4,4'-diaminobiphenyl, N,N'-diphenyl-N,N'-dinaphthyl-4,4'-diaminobiphenyl, and N,N,N',N'-tetraphenyl-21H,23H-porphyrin; triarylamine derivatives including polymers having aromatic tertiary amines in main chains or side chains thereof, 1,1-bis(4-di-p-tolylaminophenyl)cyclohexane, N,N,N-tri(p-tolyl)amine, and 4,4,'4'-tris[N-(3-methylphenyl)-N-phenylamino]trimethylamine; carbazole derivatives including N-phenylcarbazole and polyvinylcarbazole; phthalocyanine derivatives including nonmetallic phthalocyanine and copper phthalocyanine; starburst amine derivatives; enamine stilbene derivatives; derivatives of aromatic tertiary amine-containing styryl amine compounds; spirobifluorenyl anthracene; tetrafluorene; thiophene; aniline; pyrrole; and phenylene vinylene, R is selected from a group consisting of a trimethoxysilane group (—Si(OCH$_3$)$_3$), a trichlorosilane group (—SiCl$_3$), a phosphate group (—PO$_3^-$) and —P(O)(OH)$_2$, n is an integer of about 1.

2. The functionalized metal nanoparticle according to claim 1, wherein the nanoparticle is represented by Formula 7 below:

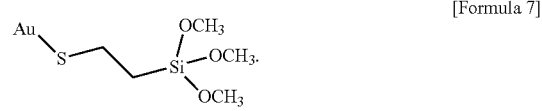

[Formula 7]

3. The functionalized metal nanoparticle according to claim 1, wherein F in the above Formula 1 is not an ethyl group.

4. The functionalized metal nanoparticle according to claim 1, wherein the R in the above Formula 1 is selected from the group consisting of a trichlorosilane group (—SiCl$_3$), a phosphate group (—PO$_3^-$) and —P(O)(OH)$_2$.

5. The functionalized metal nanoparticle according to claim 1, wherein X in the above Formula 1 is a cyano group (CN).

6. A buffer layer comprising the functionalized metal nanoparticle represented by Formula 1:

M-X—F—R$_n$ [Formula 1]

wherein M is a metal atom selected from the group consisting of gold (Au), silver (Ag), copper (Cu), palladium (Pd) and platinum (Pt), X is sulfur (S) or a cyano group (CN), F is selected from the group consisting of ethyl groups; oxadiazole compounds; porphyrin compound derivatives including N,N'-diphenyl-N,N'-di(3-methylphenyl)-4,4'-diaminobiphenyl, N,N'-diphenyl-N,N'-dinaphthyl-4,4'-diaminobiphenyl, and N,N,N',N'-tetraphenyl-21H,23H-porphyrin; triarylamine derivatives including polymers having aromatic tertiary amines in main chains or side chains thereof, 1,1-bis(4-di-p-tolylaminophenyl)cyclohexane, N,N,N-tri(p-tolyl)amine, and 4,4',4'-tris[N-(3-methylphenyl)-N-phenylamino]trimethylamine; carbazole derivatives including N-phenylcarbazole and polyvinylcarbazole; phthalocyanine derivatives including nonmetallic phthalocyanine and copper phthalocyanine; starburst amine derivatives; enamine stilbene derivatives; derivatives of aromatic tertiary amine-containing styryl amine compounds; spirobifluorenyl anthracene; tetrafluorene; thiophene; aniline; pyrrole; and phenylene vinylene, R is selected from a group consisting of a trimethoxysilane group (—Si(OCH$_3$)$_3$), a trichlorosilane group (—SiCl$_3$), a phosphate group (—PO$_3^-$) and —P(O)(OH)$_2$, and n is an integer of about 1.

7. The buffer layer according to claim 6, wherein the buffer layer includes a functionalized metal nanoparticle represented by Formula 7:

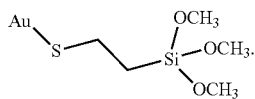

[Formula 7]

8. The buffer layer according to claim 6, wherein the buffer layer is a monolayer.

9. The buffer layer according to claim 6, wherein the buffer layer has a thickness of about 0.01 nm to about 100 nm.

10. An electronic device comprising the buffer layer according to claim 6, on a surface of electrode.

11. The electronic device according to claim 10, wherein the electronic device is selected from the group consisting of an organic thin film transistor (OTFT), an organic light emitting diode (OLED), a solar cell, and an organic photovoltaic conversion device.

12. The buffer layer according to claim 6, wherein F in the above Formula 1 is not an ethyl group.

13. The buffer layer according to claim 6, wherein the R in the above Formula 1 is selected from the group consisting of a trichlorosilane group (—SiCl$_3$), a phosphate group (—PO$_3^-$) and —P(O)(OH)$_2$.

14. The buffer layer according to claim 6, wherein F in the above Formula 1 is an oxadiazole compound.

15. A functionalized metal nanoparticle represented by Formula 1:

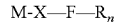

[Formula 1]

wherein M is a metal atom selected from the group consisting of gold (Au), silver (Ag), copper (Cu), palladium (Pd) and platinum (Pt), X is sulfur (S) or a cyano group (CN), F is selected from the group consisting of ethyl groups; oxadiazole compounds; porphyrin compound derivatives including N,N'-diphenyl-N,N'-di(3-methylphenyl)-4,4'-diaminobiphenyl, N,N'-diphenyl-N,N'-dinaphthyl-4,4'-diaminobiphenyl, and N,N,N',N'-tetraphenyl-21H,23H-porphyrin; triarylamine derivatives including polymers having aromatic tertiary amines in main chains or side chains thereof, 1,1-bis(4-di-p-tolylaminophenyl)cyclohexane, N,N,N-tri(p-tolyl)amine, and 4,4',4'-tris[N-(3-methylphenyl)-N-phenylamino]trimethylamine; carbazole derivatives including N-phenylcarbazole and polyvinylcarbazole; phthalocyanine derivatives including nonmetallic phthalocyanine and copper phthalocyanine; starburst amine derivatives; enamine stilbene derivatives; derivatives of aromatic tertiary amine-containing styryl amine compounds; spirobifluorenyl anthracene; tetrafluorene; thiophene; aniline; pyrrole; and phenylene vinylene, R is selected from a group consisting of a trichlorosilane group (—SiCl$_3$), a phosphate group (—PO$_3^-$) and —P(O)(OH)$_2$, and n is an integer of about 1.

* * * * *